United States Patent [19]
Luther et al.

[11] Patent Number: 5,971,957
[45] Date of Patent: Oct. 26, 1999

[54] THROUGH-THE-NEEDLE CANNULA AND SPLIT NEEDLE PLACEMENT APPARATUS AND METHOD OF USE

[76] Inventors: Ronald B. Luther, 530 Kings Rd., Newport Beach, Calif. 92663; Edward E. Elson, 4356 Claytor Cir., Anaheim, Calif. 92807

[21] Appl. No.: 09/111,559
[22] Filed: Jul. 8, 1998
[51] Int. Cl.⁶ .................................................. A61M 5/178
[52] U.S. Cl. ........................ 604/160; 604/264; 604/272
[58] Field of Search ................................. 604/160, 161, 604/239, 264, 272, 273, 274, 158

[56] References Cited

U.S. PATENT DOCUMENTS

| | | |
|---|---|---|
| D. 247,975 | 5/1978 | Luther . |
| 4,100,393 | 7/1978 | Luther . |
| 4,377,165 | 3/1983 | Luther et al. . |
| 4,401,433 | 8/1983 | Luther . |
| 4,449,973 | 5/1984 | Luther . |
| 4,702,735 | 10/1987 | Luther et al. . |
| 4,762,516 | 8/1988 | Luther et al. . |
| 4,790,817 | 12/1988 | Luther . |
| 4,950,252 | 8/1990 | Luther et al. . |
| 4,957,488 | 9/1990 | Cameron et al. . |
| 4,957,489 | 9/1990 | Cameron et al. . |

*Primary Examiner*—Ronald Stright
*Assistant Examiner*—Kent Gring
*Attorney, Agent, or Firm*—Michael J. Ram; Loeb & Loeb LLP

[57] ABSTRACT

A novel enhanced needle splitting through-the-needle cannula placement apparatus includes a hinged housing, a scored splittable needle, a needle splitting means and sliding means for facile removal of a needle while leaving the cannula within a body vessel. A method of its use is also taught.

15 Claims, 8 Drawing Sheets fig. 3 fig. 4

FIG. 14

THROUGH-THE-NEEDLE CANNULA AND SPLIT NEEDLE PLACEMENT APPARATUS AND METHOD OF USE

BACKGROUND OF THE INVENTION

1. Area of the Art

The present invention relates to medical devices and to methods for the administration and withdrawal of fluids from a patient. Particularly, the present invention relates to catheter or cannula placement devices including those which are emplaced by passing the catheter through a hollowed needle.

2. Description of the Prior Art

Catheters effective for use within the context of various medical procedures are known, and generally formed from flexible materials to enable their placement in desired locations within patients. Likewise, conventional systems for placing catheters in any number of desired positions generally rely upon needles for ingress into desired vessels.

It has become generally known that insertion of catheters may be accomplished either by coaxially mounting a catheter onto a needle (over-the-needle) or by locating a catheter inside of the lumen of a needle (through-the-needle). Prior art devices of both of these types are subject to numerous pitfalls and constraints which significantly complicate the setting up of an intravenous fluid delivery system.

Prominent among the drawbacks with through-the-needle devices is removal of the needle which is required to place the devices into patients. With a catheter or cannula disposed inside, a cannula having its proximate end housed within a needle is inserted through the skin with the appropriate placement of its tip inside of the desired blood vessel. Withdrawal of the needle leaves the catheter or cannula properly within the vessel.

In order to withdraw apparatus involved in through-the-needle catheter placement, it is important to immediately remove the needle from the assembly to minimize trauma caused to the involved patients. Likewise, known systems require that needles be removed by retracting the same upwardly along the catheter, often causing further injury and trauma to patients. Further, the needles themselves are responsible for numerous cut cannulae or catheters and subsequent loss of the catheter within the body, and have motivated aspects of the teachings of the present invention.

With a catheter located inside of the lumen of the needle, withdrawal of the needle is of prime importance once proper placement has been achieved. It is difficult to remove needles so situated owing to the gross geometrical constraints from the hub at the proximate end of the catheter.

Splitting of needles was first practiced in U.S. Pat. Nos.:

| 3,569,658; | 3,382,872; | 4,100,893; | 4,306,652; |
| 4,401,433; | 4,449,973; | 4,559,04; | and 4,610,691. |

However, each of these references disclosed rendering the needle splittable by forming the needle in two longitudinal halves, or by effecting longitudinal scoring of the same, and manipulating the entire mechanism in attempts to split the needles.

Additionally, the needles have induced damages to patients and to the intravenous assembly itself have limited the efficacy of these devices. Attempts to overcome these problems have ranged from different types of detachable needle-splitters to techniques for removing the needle assembly from the catheter once situated. Unfortunately, unwanted perforation and shearing of the external portions of catheters remains a major problem.

Prior art through-the-needle catheters and mechanisms have failed to adequately address these issues. For example, U.S. Pat. Nos. 4,957,488 and 4,957,489 which both issued to Cameron and Doman on Sep. 18, 1990 and are assigned to CRITIKON, INC., tried to arrest forward motion of a needle in combination with a rapidly deformable catheter cannula. The needle, however, continues to present difficulty on the basis of the its lack of facile extradition from the prior art devices.

Likewise, the present inventor has developed Percutaneous Port Assemblies (U.S. Pat. No. 5,569,217; issued Oct. 29, 1996), Hardened Tip over-the-needle catheters, as shown in U.S. Pat. No. 5,683,370; which issued Nov. 4, 1997 and Dual Lurnen catheters in U.S. Pat. No. 5,522,807 and 5,554,136; the latter of which was issued Sep. 10, 1996 and U.S. Pat. Nos.:

| 4,377,165; | 4,100,393; | 4,254,081; | 4,401,433; |
| 4,559,043; | 4,610,671; | 4,612,170; | 4,874,373; |
| 4,950,252; | 4,950,256; | 4,964,854; | 5,098,394; | each of which is patentably distinguishable from the teachings of the present invention.

Accordingly, although advances have been made in catheter introduction and placement technologies, clearly there exists a longstanding desire to innovate novel enhanced ways for permitting needles to be removed without concomitant damages to catheters and tissue. Although various attempts to accomplish the same have employed elaborate and circumlocuted means, it has now been discovered that significant aspects this problem can be eliminated.

OBJECTS AND SUMMARY OF THE INVENTION

Accordingly, it is a prime objective of the present invention to provide a needle splitting and emplacement apparatus which overcomes the drawbacks of the prior art.

It is another object of the present invention to provide a novel enhanced apparatus including a needle splitter having demonstrable results and benefits.

It is yet another object of the present invention to provide the above objects in a method for using a needle splitting and emplacement apparatus, whereby a multiplicity of needle gauges and cannula sizes may be effectively employed.

Briefly stated, a novel enhanced needle splitting through-the-needle catheter emplacement apparatus includes a hinged housing, a needle splitting means and sliding adjustment features for facile removal of a needle. A method of use is also taught.

According to a feature of the present invention, there is provided a needle-splitting apparatus, comprising, in combination, a grooved splitter housing, having a first and a second side, joined by means for hinging, which splitter housing is capable of being moved from a first to a second position, means for matingly engaging said first and said second side, means for holding a needle, which means is disposed within the groove located on at least one of said first and second sides when said first and said second sides are in a first position, and a pre-scored needle with a lumen disposed therein having a distal and a proximate end, wherein said proximate end is branched into first and second segments and a means for splitting said needle.

According to an additional feature of the present invention, there is provided a needle splitting through-the-needle catheter emplacement device, comprising, in combination; a splitter housing having a first and a second side, each side having an inner and an outer face, a hinge joining said first and second sides, an extended member disposed on said inner face of said first side, a projecting member disposed upon said inner face of said second side, an orifice disposed on an inner face of said second side for receiving said extended member, a needle holder for holding a longitudinally scored needle; and means for longitudinally moving the needle holder.

According to yet a still further feature of the present invention, there is provided a method for using a needle-splitting mechanism comprising the steps of: providing a longitudinally scored needle with a lumen disposed therein having a distal and a proximate end, wherein said proximate end is branched into first and second segments, fixing said needle within a recessed needle holder having a first projection; whereby said proximate end is held defining a space between said first and said second branched segments, fixing the needle holder within a grooved housing, having a hinged first and second side and at least one extending member projecting from said second side, closing the first and second side to define an integral member, whereby said at least one extending member is disposed in said space between said first and said second branched segments of said needle, placing a catheter within the lumen space of said needle, inserting said emplaced catheter into a desired location, sliding said needle holder within the needle splitting assembly by placing pressure on said first projection and moving said needle holder from a first to a second position, whereby said needle is split along said longitudinally defined axis, removing said split needle, whereby said sliding step further includes using a toothed set of ratcheted biased grooves to alternately fix and release said needle holder.

The above, and other objects, features, advantages, and innovations of the present invention will become apparent from the following description, figures, presented hereinafter in which like reference designating numerals represent common elements, in addition to the claims appended hereto defining the metes and bounds of the present invention and those equivalents under law which are at the ordinary skill level of one knowledgeable in the instant fields of art.

DETAILED DESCRIPTION OF THE INVENTION

The present inventors have discovered that a novel enhanced needle-splitting device can effectively eliminate many of the constraints typically associated with removal of needles from cannula and catheter delivery assemblies.

The present inventors have also discovered that an improvement in the construction of a through-the-needle type of catheter assembly can include a novel needle splitting function.

Figure 1:
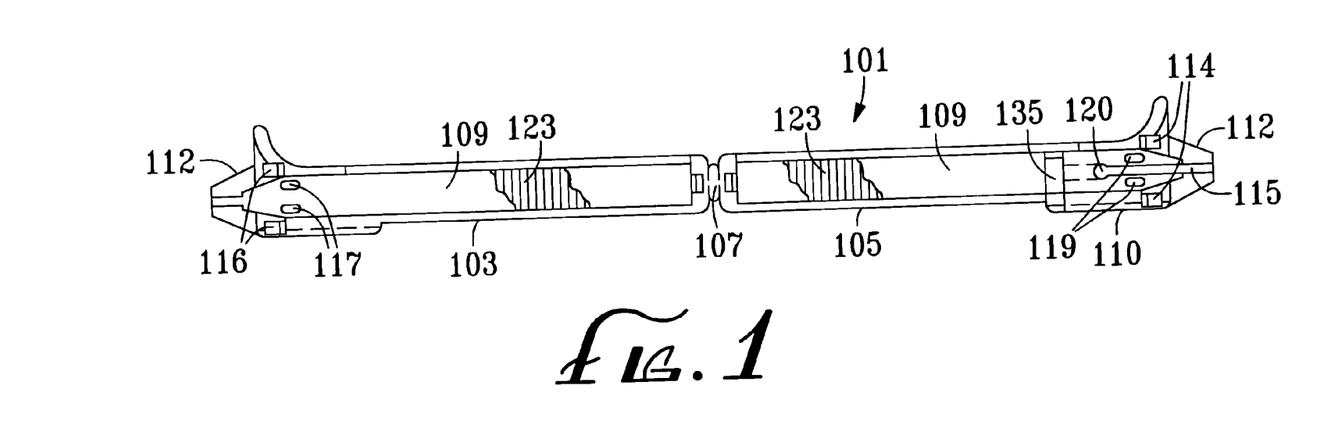
FIG. 1 is a front view of a first embodiment of the apparatus of the present invention with a hinge mechanism in an extended position showing the internal surface of the device.

Referring now to FIG. 1, there is shown a view a first embodiment of the present invention defined generally by splitter housing 101, which includes first side 103 and second side 105.

A hinging means 107 joins the first side 103 with the second side 105. In the embodiment shown, the hinging means 107 is a flexible plastic portion of the unit integral with the first and second side 103, 105, usually referred to as a living hinge. Extending along the length of the internal surface of each of the first and second side 103, 105 is a groove 109, the function of which will be discussed hereinbelow. The grooves terminate, at the end of each side 103, 105 distant from the hinging means 107, in a shoulder 110 which further includes a nose, or needle guide, 112 extending longitudinally therefrom. Projecting upward from one shoulder 110 is at least one extended member 114 which locks into matching openings 116 in the second shoulder to hold the device 101 in its closed configuration. Located at the shoulder 110 end of one of the grooves 109 is a pair of extensions 117, which function to split the needle, these extensions 117 resting within matching orifices 119 at a similar location on the other groove when the device 101 is in its closed configuration. One end of the device, shown in FIG. 1 to be on the first side 103, is adapted to receive the splittable needle 113 while the other end of the device 101, shown in FIG. 1 to be on the second side 105 is adapted, by inclusion of an open channel 115 and port 120, to receive the catheter 118 to be placed using the placement device. While the various different components are shown on the first or second side 103, 105 one skilled in the art will recognize that they, or half of a pair, can be located on either side as long as the fully assembled device functions in the same manner.

Figure 2:
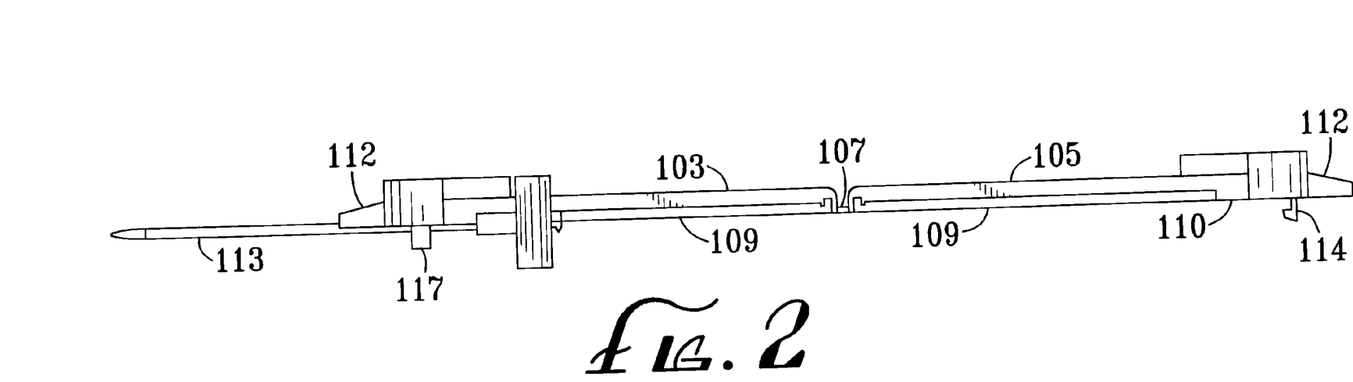
FIG. 2 is a side view showing the apparatus illustrated in FIG. 1, with needle installed, in its extended configuration.
Figure 3:
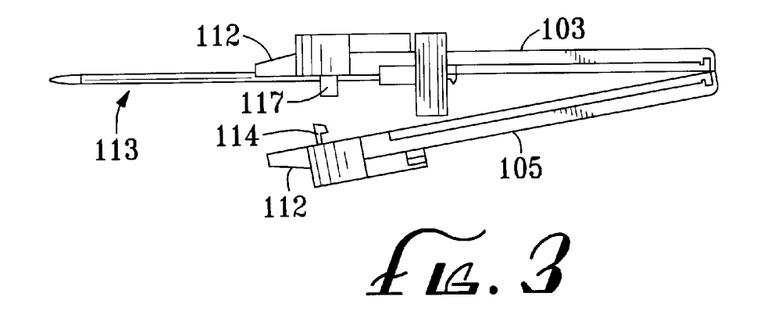
FIG. 3 is a top view of the apparatus of FIG. 1 in a partly folded configuration.
Figure 4:
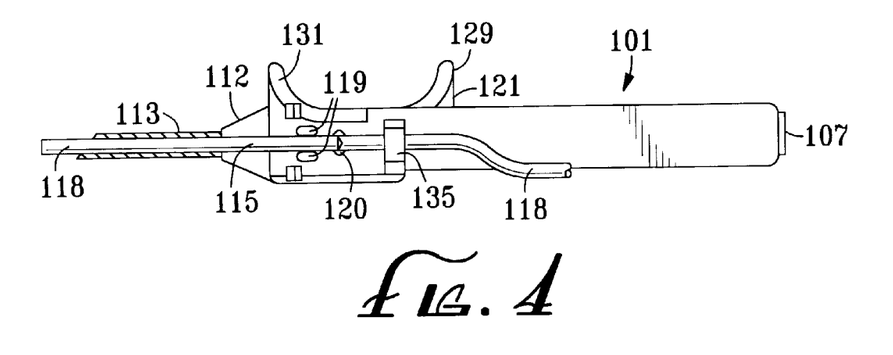
FIG. 4 is a side view of the apparatus illustrated in FIG. 1 with the respective halves secured together to show the embodiment in its operative form with needle cutaway to reveal the cannula within.

Referring to FIGS. 2, 3 and 4 first side 103 is moved from a first open position (FIG. 2) to a second or partly closed position (FIG. 3) to a third closed position (FIG. 4) whereby extended members 114 become lodged in matching openings 116 and extensions 117 rest in orifices 119. The needle 113 is housed within first side 105 and becomes disposed between first side 103 and second side 105 with extensions 117 resting within the split opening 122 of the needle assembly such that a catheter may be extended therethrough as shown in FIG. 4.

Referring to FIG. 4, a detailed view of second side 105 is shown whereby port 120 receives a cannula or catheter 118 to be emplaced within the body and allows the same to be disposed within the lumen of needle 113. Needle 113 is thus held in place by needle holder 121, biasing the split opening 122 of the needle 113 against the extensions 117 on the inside of either first side 103 or second side 105 (see FIG. 8).

Referring again to FIG. 1, first side 103 and second side 105 are shown separated, or in a first position. Teeth 123 are disposed throughout the grooved portion as fully shown in FIG. 6 and FIG. 7 (only partially shown in FIG. 1 for clarity), enabling needle holder 121 (see FIG. 5–FIG. 7) to travel, in ratcheted fashion from one end of the splitter housing to the other. The teeth 123 are angled and interact with a second set of teeth 125 on the needle holder 121 to prevent moving forward, i.e., reextending the needle, after it has been withdrawn and split.

Figure 5:
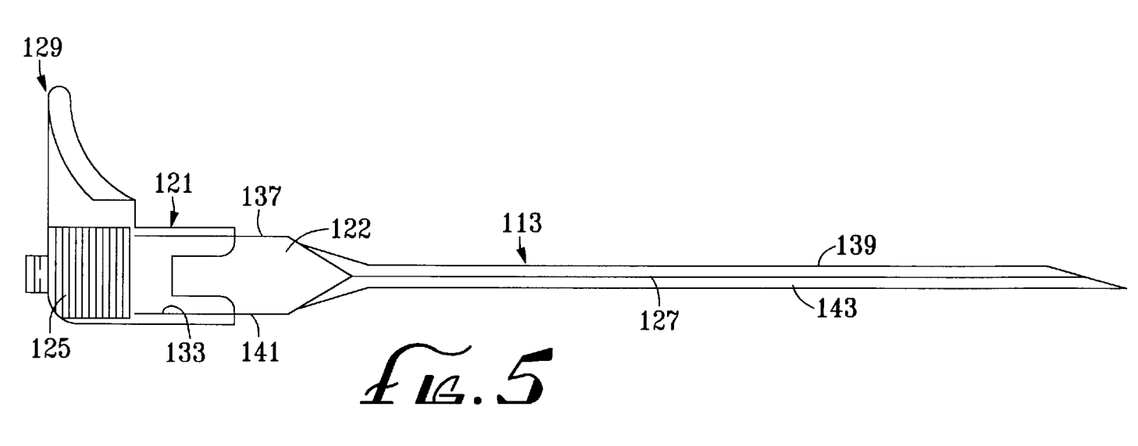
FIG. 5 illustrates an unsplit needle and needle holder used in the apparatus of the present invention.

Referring to FIG. 5, a detailed view of needle holder 121 is shown, with the second set of teeth 125 which are effective for engaging the first set of teeth 123 in the groove, the teeth 123, 125 engaging with each other to allow movement of the needle holder 121 in only one direction along the grooved portion between first side 103 and second side 105. Needle 113 includes longitudinal scoring 127 (a second longitudinal scoring 127, not shown, is 180° from the shown scoring) which allows the needle 113 to be forced apart at the scoring 127 by extensions 117 as needle holder 121 with needle attached is ratcheted away from the tip of needle 113, i.e., pulled down the length of the groove 109. As shown in the drawings, the longitudinal scoring, in contrast with the prior art devices, is along both sides of the needle (at 90° and 270° when viewed from the end) rather than on the top and bottom (0° and 180°) of prior devices. The scoring on prior art devices splits the point of the needle making fabrication difficult and producing a very sharp pair of points on the split needle which increases the possibility of damaging the cannula. Finger grip 129 allows a user to put moving pressure on needle holder 121 and to ratchet the same along the length of the splitter housing 101 in order to separate needle 113 to facilitate the facile withdrawal of the same during use without cutting the cannula.

Figure 6:
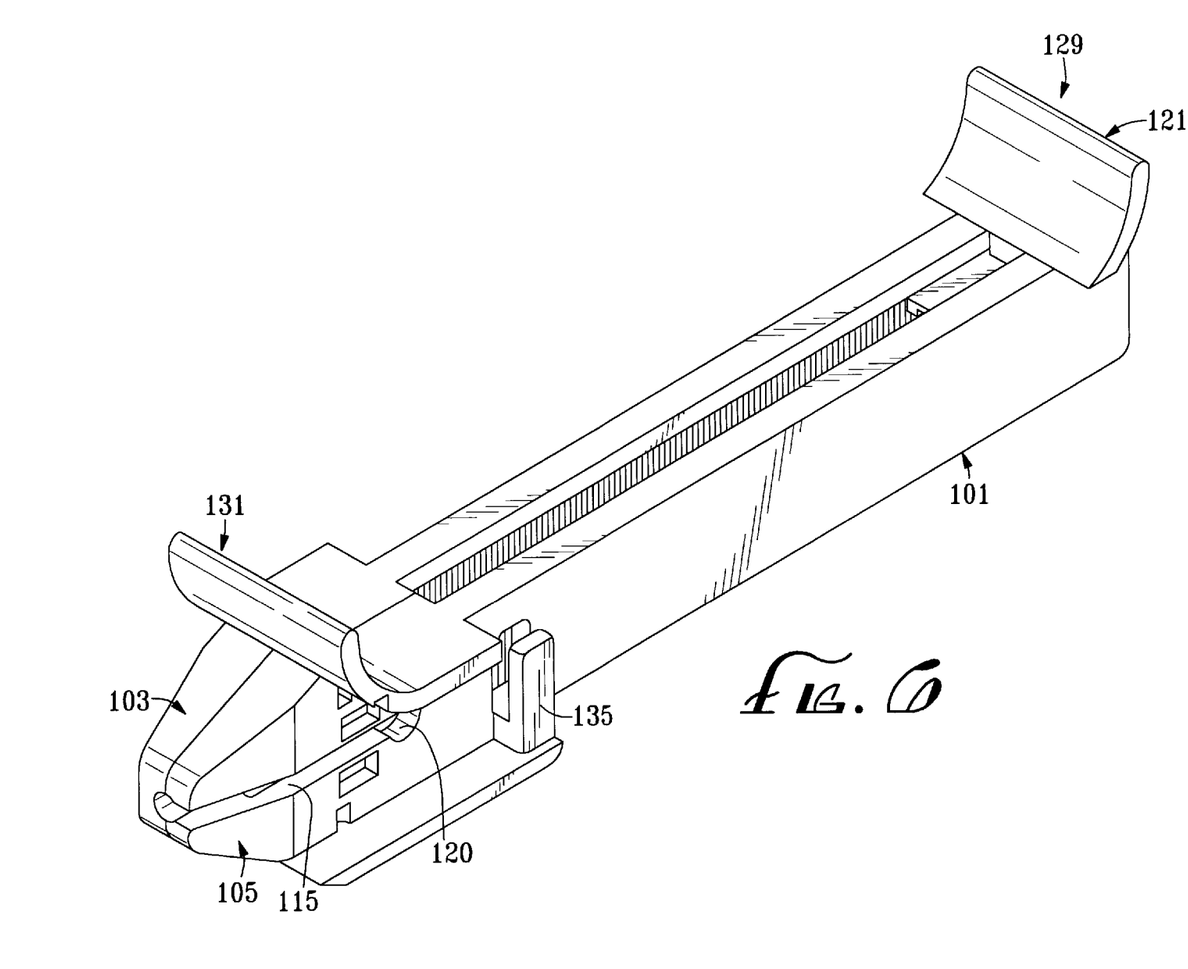
FIG. 6 is a top perspective view of the embodiment of FIGS. 1–4 with the needle fully retracted into the apparatus so that it is not visible.

Referring now to FIG. 6 splitter housing 101 is shown with first side 103, and second side 105 snapped together. Needle holder 121 is within the housing 101 but the only portion visible is the finger grip 129 as the needle holder 121 is shown in its fully retracted position with the needle 113, now split, residing fully inside the groove 109. A second projection 131 formed by two extensions on top of the first and second sides 103, 105 consists of a combination of the two extensions. The second extension 131 assists the user in gripping the splitter housing 101 while the needle holder 121 is being retracted.

Figure 7:
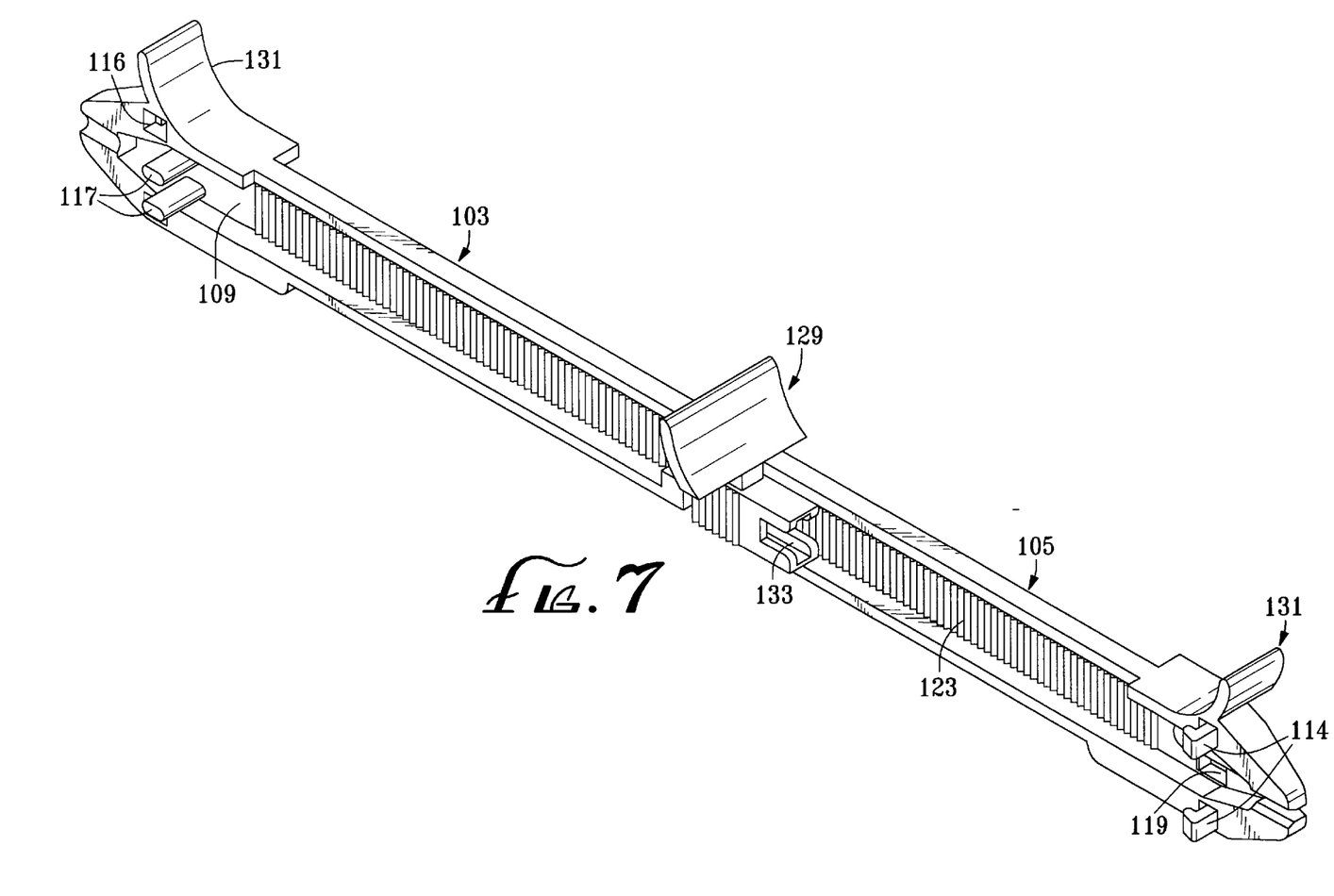
FIG. 7 is a top perspective view of the embodiment of FIGS. 1–4, without needle, with the respective halves in the open position.

Referring to FIG. 7, first side 103 and second side 105 are shown in the open position. Recess 133 on the needle holder 121 is shown wherein the internal, split end of needle 113 (not shown in this view) is housed. Likewise, extensions 117 are shown disposed inside of the groove 109 and openings 116 are shown on the shoulder 110 on first side 103, while extended member 114, mounted upon the shoulder and orifices 119 in the groove 109 are illustrated on second side 105.

According to the teachings of the present invention a variety of needle sizes (gauges) are both effective and appropriate for use with various cannula sizes. A representative sample of those sizes, along with appropriate cannula sizes which have been used with the apparatus of the present invention, are listed within TABLE 1, below.

| ISO Needle and Catheter OD's & ID's in Inches | | | | | |
|---|---|---|---|---|---|
| | Needle | | Catheter | | |
| Gauge | OD | ID | OD | ID | Wall |
| 28 | .029 | .023 | .021 | .013 | .004 |
| 24 | .037 | .031 | .029 | .019 | .005 |
| 22 | .045 | .039 | .037 | .025 | .006 |
| 20 | .053 | .047 | .045 | .033 | .006 |
| 18 | .061 | .056 | .054 | .042 | .006 |
| 16 | .080 | .074 | .072 | .058 | .007 |

Figure 8:
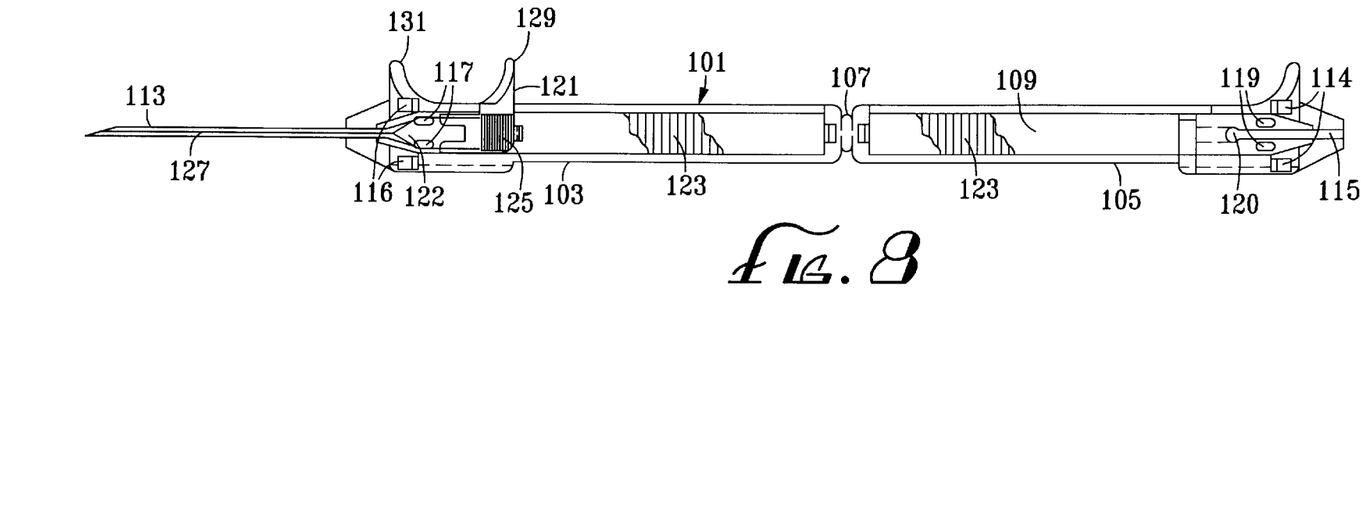
FIG. 8 shows a side view of the needle holder as shown in FIG. 1 and FIG. 2 with needle in place.

In order to use the above described embodiment the splitter housing is placed on a flat surface in the manner shown in FIG. 1 and the needle holder 121 with desired size needle 113 as shown in FIG. 5 is placed in the housing 101 to produce the assembly as shown in FIGS. 2 and 8 with both extensions 117 located within the split opening between the two ends of the upper and lower half of the splittable needle 113. The housing is then folded at the hinging means 107, as shown in FIG. 3 until the first side 103 and second side 105 come in contact and the extended members 114 snap into the openings 116, holding the housing in its closed and ready to use configuration. This causes the top ends of the extensions 117 to rest in the orifices 119, trapping the split needle in its desired position for placement in a blood vessel. Referring to FIG. 4, the distal end of the appropriately sized catheter 118 is inserted through port 120, which positions it within the split opening, and threaded along at least a portion of the length of the needle 113 but not past the open pointed end of the needle 113 and the portion of the catheter immediately exterior of the port 120 is placed under clip 135 for temporary retention. The catheter placement device is now ready for use.

The assembled device is then used in the manner typical of a through-the-needle delivery system. The skin is penetrated by the needle and once the needle tip is verified as being located within the desired vein or artery the cannula is fed through the needle into and along the punctured vessel to the desired length. The needle can then be withdrawn from the puncture site by withdrawing the needle into the splitter housing which simultaneously splits the needle and withdraws it from the puncture site. To split the needle the splitter housing is stabilized so as not to cut the catheter 118 with the sharp pointed end of the needle and, grasping the first projection 129 and the second projection 131, the first projection 129 is pulled along the groove 109 toward the hinging means 107 and away from the second projection 131. This causes the extensions 117 to force apart the top and bottom halves of the needle 113 along the longitudinal scoring 127 without disturbing the catheter 118 which resides within the needle 113. When the first projection 129 reaches the end of the groove 109 nearest the hinging means 107 the needle is completely split in half along its length and resides completely within the split housing assembly and the sharp end of the needle is isolated from the catheter surface. The catheter can then be taped to the skin at or near the puncture site and the splitter housing removed from the catheter by pulling the cannula up through the open channel 115 and releasing it from under clip 135.

FIGS. 9–18 show two versions of a second embodiment of the through-the needle cannula delivery system which incorporates features of the invention. Like parts have the same reference numbers as in the first embodiment The major differences between the embodiments is replacement of the pair of extensions 117 by a single wedge shaped needle splitter 217, replacement of the pair of extension members 114 by a single retaining member 214 located within the groove 109, replacement of the first set of teeth 123 along the length of the groove 109 by two ratchet stops 223, the addition of a roller 250 to the outer surface of the splitter housing 201 to assist in controlling the feeding of the catheter 118 into the needle 113, and the use of a lower profile needle holder 221.

Figure 12:
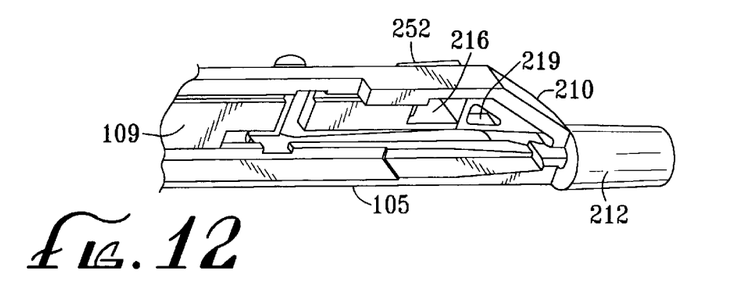
FIG. 12 is a perspective view of a right portion of a second version of the second embodiment of the cannula delivery system showing the internal structure thereof.
Figure 13:
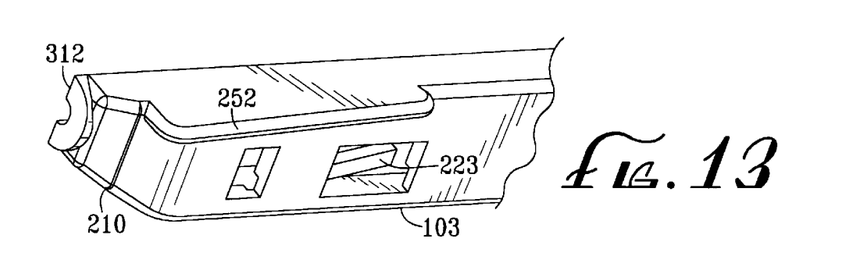
FIG. 13 is a perspective view of the left portion of the second version of the second embodiment shown in FIG. 11 showing the external structure thereof.
Figure 14:
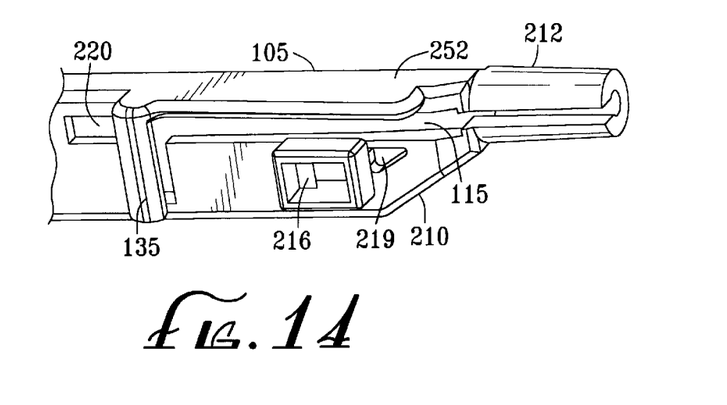
FIG. 14 is a perspective view of the right portion of the second version of the second embodiment shown in FIG. 12 showing the external structure thereof.
Figure 15:
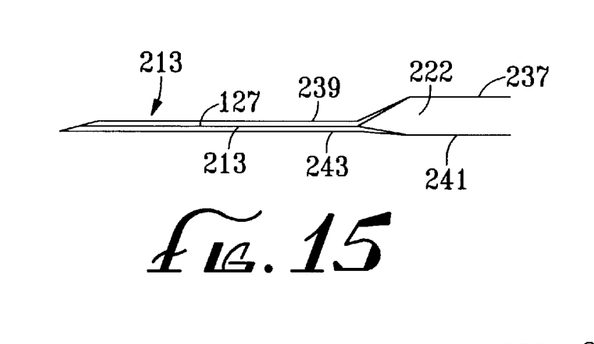
FIG. 15 is a side view of the splittable needle for use in the second embodiment.

The primary difference between the first and second version of the second embodiment is that the first version has a needle guide 112 split longitudinally down the middle, such as in the first embodiment, so that a first longitudinal half of the needle guide 112 is on the first side 103 and the second longitudinal half is on the second side 105 while in the second version substantially all of the needle guide 212 is on one of the sides, the second side 105 as shown in FIGS. 12 and 14, and a much shortened portion thereof is located on the end of the other (the first) side 103.

The needle 213 and needle holder is also slightly modified from that used in the first embodiment. In the first embodiment, referring to FIG. 5, the upper leg 137, which is an extension of the upper half 139 of the splittable needle attachable to a first portion of the needle holder 121, and the lower leg 141, which is an extension of the lower half 143 of the splittable needle which is attachable to the another portion of the needle holder 121, are approximately equally spaced from a center line extending down the axis of the lumen of the needle. In both versions of the second embodiment the lower leg 241 extends away from the body of the needle at a level slightly further from the central axis then the outer diameter of the needle while the upper leg 237 is spaced a much greater distance from the axis then the lower leg 241 while maintaining the distance between the two legs 237, 241 to substantially the same distance as in the first embodiment as shown in FIG. 5.

Figure 18:
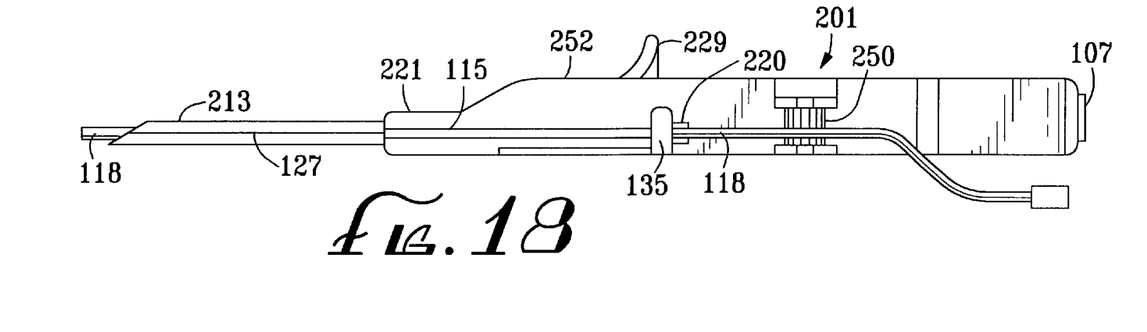
FIG. 18 is a side view of the assembled second embodiment of the cannula delivery device shown in FIG. 17 with catheter added.

The combination results in a splitter housing 201 with the center line of the needle, as best shown by comparison of FIG. 18 with FIG. 4, being closer to the lower surface of the housing. This allows the needle to enter the vessel being punctured at a lower angle, thus reducing the possibility of the needle also puncturing the opposite side of the vessel.

Figure 9:
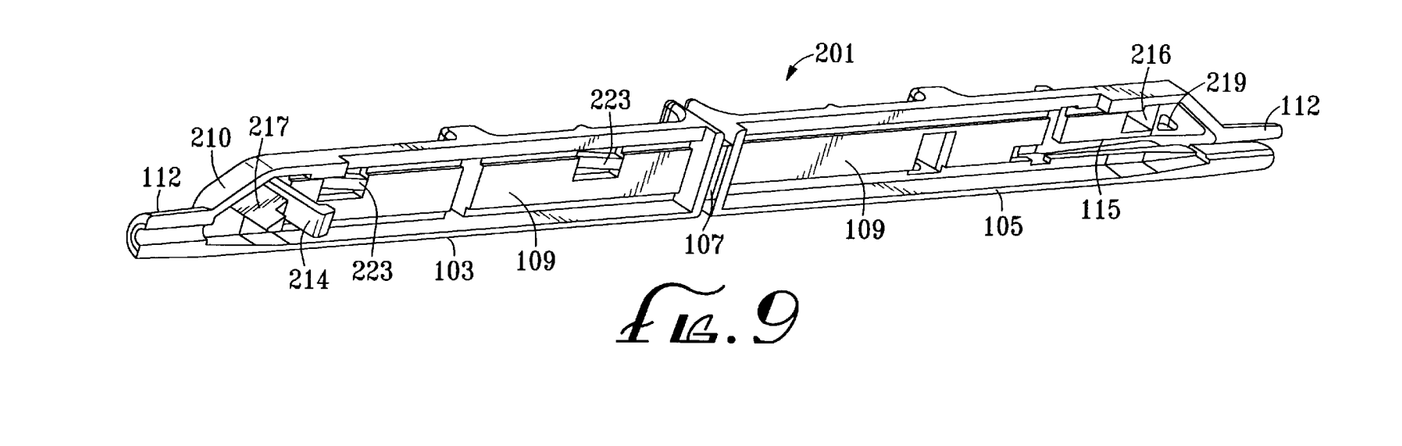
FIG. 9 is a perspective view of a first version of a second embodiment of a cannula delivery system showing the internal structure of the device.
Figure 10:
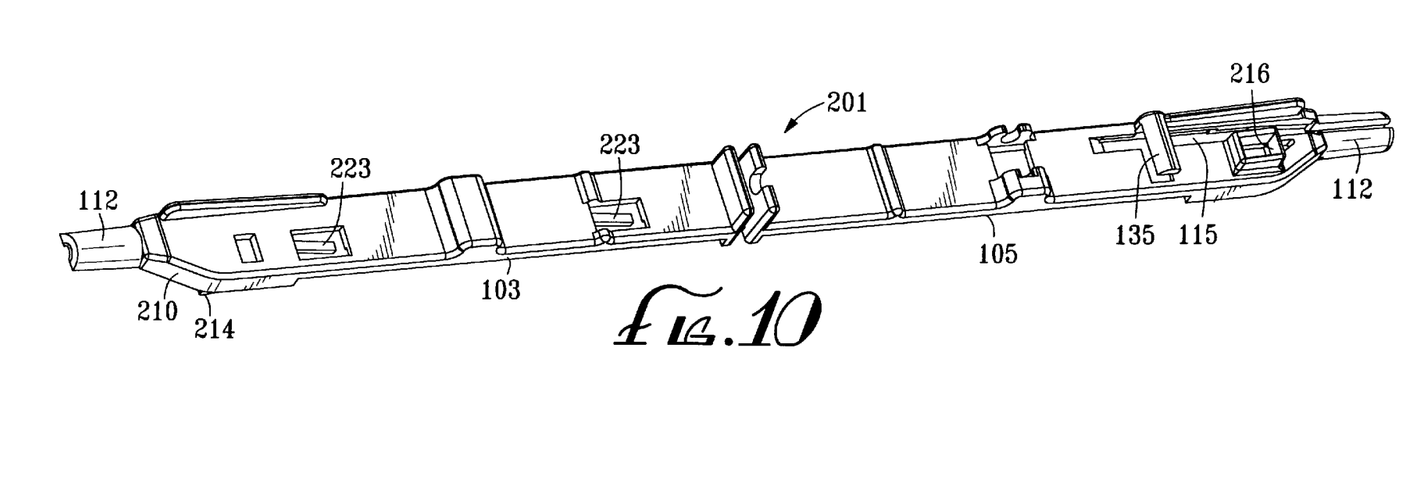
FIG. 10 is a perspective view of the embodiment shown in FIG. 10 showing the external structure thereof.
Figure 11:
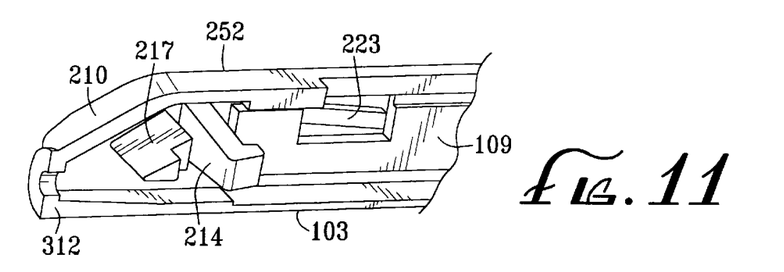
FIG. 11 is a perspective view of a left portion of a second version of the second embodiment of the cannula delivery system showing the internal structure thereof.

With specific reference to FIGS. 9–10, there is shown an inside and outside perspective view of the second embodiment consisting of a splitter housing 201, which includes first side 103 and second side 105.

A hinging means 107 is shown as a bendable plastic extension joining the first side 103 with the second side 105.

Extending along the length of each of the first and second side 103, 105 is a groove 109. The grooves and the sides terminate, at the end of each side 103, 105 distant from the hinging means 107, in a tapered end 210 which further includes a nose, or needle guide, 112 extending longitudinally therefrom. Projecting upward from the groove 109 near the one nose is a retaining member 214 which locks into matching opening 216 in the second side 105 in the groove at a similar location so as to hold the device 101 in its closed configuration when the first and second side 103, 105 are brought together by bending at the hinging means 107. Also located at the same end of the side at a point between the retaining member 214 and the nose of the tapered end 10 is a needle splitter 217, in the shape of a wedge with a forward edge pointing towards, but being above the line of the inner surface of the needle holder 112. As the needle holder 221 is drawn along the length of the splitter housing 201 toward the hinging means 107 the wedge shaped needle splitter 217 forces the upper leg 237 upward causing a split to propagate along the length of the longitudinal scoring 127 and down the length of the needle 213. The upper surface of the needle splitter 217 rests within a matching orifices 219 at a similar location on the other side 105 when the device 201 is in its closed configuration. One end of the device, shown in FIGS. 9 and 10 to be on the first side 103, is adapted to receive the splittable needle 213 while the other end of the device 201, shown in FIGS. 9 and 10 to be on the second side 105 is adapted, by inclusion of an open channel 115, to receive the catheter 118 to be placed using the placement device. Again, while the various different components are shown on the first or second side 103, 105 one skilled in the art will recognize that they can be located on either side as long as the fully assembled device functions in the same manner.

In a manner similar to FIGS. 2 and 3, first side 103 is moved from a first open position (FIG. 2) to a second or partly closed position (FIG. 3) to a closed position (FIGS. 17 and 18) whereby retaining member 214 becomes lodged in matching openings 216 and needle splitter 217 rest in orifice 219. The needle 213 is housed within first side 103 and becomes disposed between first side 103 and second side 105 with needle splitter 217 resting within the split opening 222 of the needle holder 221 such that a catheter or cannula may be extended therethrough as shown in FIG. 18

Figure 16:
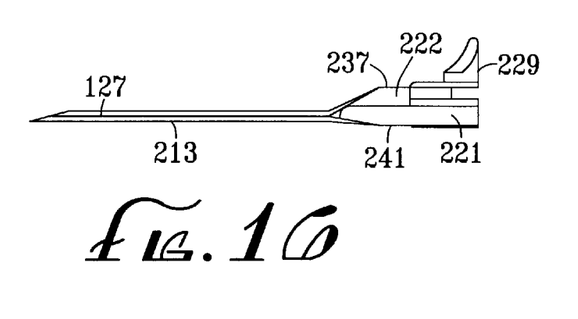
FIG. 16 is a side view of the splittable needle attached to the needle holder for use in the second embodiment.
Figure 17:
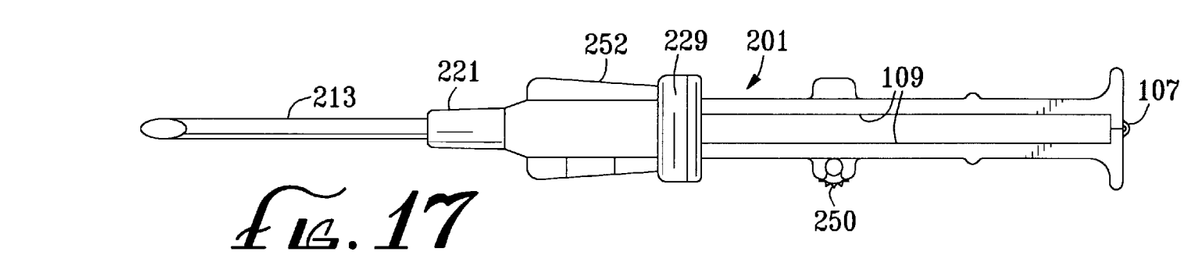
FIG. 17 is a top view of the assembled second embodiment of the cannula delivery device.

FIGS. 17 and 18, are a top and side view of the splitter housing 210 and needle holder 221 in assembled configuration. In FIG. 18 the catheter 118 is shown threaded through the port 220 and through the needle 213. Needle 213 is thus held in place by needle holder 221, biasing the split opening 222 (see FIG. 16) against a top sloped surface of the needle splitter 217.

Referring again to FIGS. 9 and 10, first side 103 and second side 105 are shown separated, or in a first position. Two ratchet stops 223 are disposed at two separated locations along the groove 109, enabling needle holder 221 to travel along the groove 109 with movement in the reverse direction being prevented by interaction between one of the ratchet stops 223 and a leading edge of the needle holder 221.

Referring to FIGS. 16 and 17, a detailed view of the needle 213 and needle holder 221 is shown, Needle 213 includes longitudinal scoring 127 (a second longitudinal scoring 127, not shown, is 180° from the shown scoring) which allows the needle 213 to be forced apart at the scoring 127 by needle splitter 217 as needle holder 221 is pulled down the length of the groove 109 toward the hinging means 107. Finger grip 229 allows a user to put moving pressure on needle holder 221 and, while grasping the splitter housing 201 near its forward end 252, to move the same toward the rear of the splitter housing 201 to separate needle 213 to facilitate the facile withdrawal of the same during use without cutting the cannula.

Referring now to FIGS. 17 and 18 splitter housing 201 is shown with first side 103, and second side 105 snapped together. Needle holder 221 is enclosed within the assembled device with the needle 213 and the finger grip 229 being visible in the assembled device before use. Also shown in FIG. 18 is the catheter 118 inserted through entry port 220 in the second side 105 of the splitter housing 201 where it passes through the split opening 222, into the lumen of the needle 213 and out the pointed end of the needle. One skilled in the art will recognize that prior to placement of the needle through the skin and into the vessel, the catheter 118 tip is fully within the needle lumen or, as an alternative the catheter 118 is not inserted into the splitter housing 201 until the puncture is completed. Thus FIG. 18 shows the needle splitter 201 and catheter 218 combination once the needle is in the vein or artery, the catheter 118 has been partly advanced and the splitting of the needle 213 has not yet commenced.

With one exception, described below, the second embodiment is operated in the same manner, described above, as the first embodiment. Referring to FIG. 18, the second embodiment includes roller 250 mounted to the outer surface of the second side 105 in the space between the part 220 and the hinging means 107 along the normal line of travel of a catheter 118 being fed into the port 220. In its preferred design, the outer surface of the roller 250 is roughened or grooved. As the cannula or catheter 118 is fed through the needle 213, the catheter 118 can be placed between the roller 250 and the finger of the operator feeding the catheter 118. By placing slight downward pressure on the catheter 118 over the roller 250 and forward pressure the roller 250 aids in feeding the catheter 118 through the needle 213.

FIGS. 11–14 show the forward end 252 of side 103 and second side 105 for the second version of the second embodiment. In this version substantially all of the needle guide 212 is formed on one end of the second side 105 of the slitter housing 201, as shown in FIGS. 12 and 14, with a much shorter half of the needle guide 312 being a part of the other side. The entry port 220, open channel 115, which extends into the needle guide 212, and clip 135 are best shown in FIG. 14. The second version is operated in the same manner as the first version.

Although the present invention has been described in considerable detail with reference to certain preferred versions and uses thereof, other versions and uses are contemplated. For example, while two score lines are shown along the length of the needle the same effect can be accomplished by a score line along only the side of the needle from which the cannula enters the needle such that withdrawing the needle along the splitter assemble causes the needle to separate and pass around the cannula without damaging same. Also features of one embodiment, such as the roller of the second embodiment, can be incorporated in the other embodiment. Therefore, the spirit and scope of the appended claims should not be limited to the description of the preferred versions contained herein.

What is claimed is:

1. A needle-splitting apparatus, comprising, in combination:
   a splitter housing having a first and a second side joined by hinging means, said first and second side being capable of being moved from an open to a closed position;
   means for matingly engaging said first and said second sides in said closed position;
   a needle holder being disposed within a groove located on at least one of said first and second sides when said first and said second sides are in the closed position; and,
   a splittable needle with a lumen disposed therein, said needle having a distal and a proximate end, wherein said proximate end is branched into first and second legs, said first and second legs being attached to the needle holder, and
   means for splitting said needle integral with at least one of said first or second sides,
   the needle being split by sliding the needle holder and attached splittable needle from a first end to a second end of the splitter housing when the splitter housing is in the closed position.

2. An apparatus according to claim 1, where the lumen in the needle is sized to allow a catheter to pass therethrough, and includes at least one score line along the length of the needle, said score line being parallel to the direction of travel of the catheter therethrough.

3. An apparatus according to claim 1, said means for matingly engaging further comprising at least one orifice, extending through said first side of said splitter housing, and at least one extended member disposed upon said second side, whereby said extended member enters into the orifice when said at least first one side of said splitter housing is moved from an open to a closed position and acts to hold the sides in the closed position.

4. An apparatus according to claim 2, wherein the means for splitting comprises at least one projecting member, disposed inside said first side of said splitter housing such that the first and second legs of the needle are disposed on opposite sides of, and in contact with, said projecting member such that movement of the needle holder along the length of the closed needle splitting apparatus causes the needle to split along said at least one score line.

5. An apparatus according to claim 1, wherein said needle holder has two recesses, one leg being received in each recess, and a projection extending outside of said splitter housing when in its closed position, said projection providing a means for moving the needle holder within the needle splitting apparatus.

6. An apparatus according to claim 1, wherein said needle splitting apparatus includes means on an inner surface of at least one of said first and second sides which cooperate with the needle holder to retard forward movement of the needle in the apparatus.

7. An apparatus according to claim 1 further including an opening through one of said sides for introduction therethrough of a catheter, said catheter being capable of passing along the length of the lumen in the needle.

8. An apparatus according to claim 7 including passage means within one of said sides which allows separation of the needle splitting apparatus from the catheter after the splittable needle has been withdrawn into the needle splitting apparatus.

9. An apparatus according to claim 7 further including catheter feeding means attached to an external surface of the side adjacent the opening, through said side for introduction of the catheter.

10. A needle splitting through-the-needle catheter placement device, comprising, in combination:
   a splitter housing having a first and a second side, each side having an inner and an outer face, said first and second sides being joined at an end thereof by hinge;

locking means for joining said first and second sides in contact along their length with a space there between; and the inner surfaces of the sides facing each other;

at least one projecting member disposed upon said inner face of said at least one side;

an orifice disposed on an inner face of the other side for receiving said projecting member;

a needle holder with attached longitudinally scored needle, said needle holder sized to fit in the space between the first and second side in a longitudinally movable manner with the needle extending beyond the splitter housing, and the projecting member located in a space between the needle housing and attached needle, and means for longitudinally moving the needle holder within the placement device toward the hinge.

11. Apparatus according to claim 10, wherein said means for longitudinally moving the needle holder further comprises:

a grooved portion extending along said respective inner faces of said first and said second sides;

means along at least one of said grooved portions which interact with the needle holder to limit movement of the needle holder away from the hinge once the needle holder has been moved toward the hinge;

means on the needle holder to interact with the means along the grooved portions to prevent movement away from the hinge;

a first projection, contiguous with the needle holder for sliding said needle holder along said grooved portion.

12. A method for placing a catheter in a vessel within the body of a patient comprising the steps of:

providing a needle having at least a longitudinal score and a lumen disposed therein having a pointed distal end and a proximate end, wherein said proximate end is branched into first and second legs;

attaching the needle to a needle holder having a first projection; whereby said proximate end defines a space between said first and said second legs and the needle holder;

placing the needle holder against a first side of a housing, said housing having a hinged first and second side and at least one extending member projecting from said second side;

closing the first and second side with the needle holder disposed between the first and second side, whereby said at least one extending members is disposed in a space between said first and said second legs of said needle and the needle holder;

placing a catheter through a wall of one of said sides into the space between the legs and then through the lumen of said needle;

causing the pointed distal end of the needle to pierce into a vessel in the body of the patient;

moving the catheter along the lumen of the needle and inserting said catheter into a desired location;

sliding said needle out of the vessel by holding the first and second side in fixed relationship to the body of the patient and placing pressure on said first projection to move said needle holder from a first to a second position, whereby said needle is withdrawn from the body and split along said longitudinally defined score, the catheter being retained in the vessel, and removing said split needle and integral member from around the catheter.

13. The method according to claim 12, whereby said sliding step further includes using interacting means on the sides and the needle holder to limit forward movement of the needle.

14. The method of claim 12 whereby moving the catheter along the lumen of the needle and into the vessel is aided by feeding means on a side of the housing adjacent the point of entry of the catheter into the housing.

15. A needle splitting through-the-needle catheter placement device, comprising, in combination:

a splitter housing having a first and a second side, each side having an inner and an outer face;

means for joining said first and second sides in contact along their length with a space there between and the inner surfaces of the sides facing each other;

a needle holder with attached longitudinally scored needle, said needle holder sized to fit in the space between the first and second side in a longitudinally movable manner with the needle extending beyond the splitter housing, and rotating means mounted to the first side to assist in feeding a catheter through a wall of the first side and through the length of this longitudinally scored needle.

* * * * *